United States Patent
Martínez Gómez

(10) Patent No.: US 11,441,083 B2
(45) Date of Patent: Sep. 13, 2022

(54) DILUENT AND DISPERSING FORMULATIONS FOR THE RECOVERY OF PETROLEUM AND METHOD FOR THE RECOVERY OF PETROLEUM FROM OIL WASTE

(71) Applicant: AMG DE COLOMBIA LIMITADA, Bogotá (CO)

(72) Inventor: Antonio Alberto Martínez Gómez, Bogotá (CO)

(73) Assignee: AMG de Colombia S.A.S., Tocancipa (CO)

(*) Notice: Subject to any disclaimer, the term of this patent is extended or adjusted under 35 U.S.C. 154(b) by 105 days.

(21) Appl. No.: 16/630,004

(22) PCT Filed: Jul. 9, 2018

(86) PCT No.: PCT/IB2018/055043
§ 371 (c)(1),
(2) Date: Jan. 10, 2020

(87) PCT Pub. No.: WO2019/012405
PCT Pub. Date: Jan. 17, 2019

(65) Prior Publication Data
US 2020/0407648 A1    Dec. 31, 2020

(30) Foreign Application Priority Data
Jul. 11, 2017 (CO) .......................... NC2017/0006973

(51) Int. Cl.
*C10G 33/04* (2006.01)
*C09K 8/584* (2006.01)

(52) U.S. Cl.
CPC .............. *C10G 33/04* (2013.01); *C09K 8/584* (2013.01); *C10G 2300/208* (2013.01)

(58) Field of Classification Search
CPC .... C10G 33/04; C10G 2300/208; C09K 8/52; C09K 8/584; C09K 8/602; C07C 7/00; C07C 7/10; E21B 43/16
See application file for complete search history.

(56) References Cited

U.S. PATENT DOCUMENTS 3,885,628 A * 5/1975 Reed ...................... E21B 43/16
                                                          166/252.1
5,897,767 A    4/1999 Patel
(Continued)

FOREIGN PATENT DOCUMENTS

CA       2708368 C      6/2016
MX    2010012348 A      5/2012
(Continued)

OTHER PUBLICATIONS

Jafarinejad, Shahryar; Petroleum Waste Treatment and Pollution Control; Chp 7 (Elsevier; 2017).

*Primary Examiner* — Brian A McCaig
(74) *Attorney, Agent, or Firm* — The Morales Law Firm; Joseph L. Morales

(57) ABSTRACT

The invention relates to a formulation for the diluting and dispersing of oily residues for the recovery of crude oil in processes for producing petroleum, comprising surfactant elements, as well as the process for recovering crude oil using a method for diluting and dispersing the oily residues generated in the petroleum production process.

12 Claims, 2 Drawing Sheets

(56) References Cited

U.S. PATENT DOCUMENTS

| | | | |
|---|---|---|---|
| 6,593,279 B2 | 7/2003 | Krosigk et al. | |
| 2011/0282125 A1 | 11/2011 | Noe et al. | |
| 2016/0102239 A1* | 4/2016 | Pietrangeli | E21B 43/16 |
| | | | 166/312 |
| 2017/0198204 A1* | 7/2017 | Nguyen | C09K 8/58 |

FOREIGN PATENT DOCUMENTS

| | | |
|---|---|---|
| RU | 2008101553 A | 7/2009 |
| WO | 2007108573 A1 | 9/2007 |
| WO | 2008130214 A1 | 10/2008 |

\* cited by examiner

DILUENT AND DISPERSING FORMULATIONS FOR THE RECOVERY OF PETROLEUM AND METHOD FOR THE RECOVERY OF PETROLEUM FROM OIL WASTE

FIELD OF THE INVENTION

The present invention is related to the field of oil recovery processes from oily waste.

BACKGROUND OF THE INVENTION

The process of surface oil production consists of the processing of fluids from the reservoir to which a treatment is applied in order to obtain specific parameters that allow its sale or final disposal, according to the applicable regulations.

In said process, the so-called production facilities are used, which comprise a series of specific equipment that allow the proper treatment of the fluids from the oil field. The main function of the production facilities is the separation and processing of fluids from the oil field (water, oil, and gas) either for sale or final disposal, according to the regulations applicable to each case. During this process, the so-called oily waste is generated, either by the result of the production treating chemicals, maintenance of facilities, line drains, or contingencies due to oil spills.

The oily waste, as a term used in the oil industry, refers to semi-liquid waste coming from industrial processes and treatment of waste water from crude oil production. This waste is considered hazardous and is characterized by the stability of the emulsion of water, solids, hydrocarbons, and metals. The stability of the emulsion depends on several factors, such as emulsifying agents (asphaltenes, resins, paraffins, and organic acids soluble in petroleum), viscosity, API (American Petroleum Institute) gravity, percentage of water, stirring, water drop size, pH, and finally the age of the emulsion.

Oily waste has traditionally undergone the following final disposal treatments: surface discharge, subsoil injection, burial, safe dumping, stabilization—solidification—encapsulation, incineration, oxidation, and bioremediation (Jafarinejad, Shahryar. Petroleum Waste Treatment and Pollution Control; Elsevier; 2017).

However, before carrying out such treatments, the oily waste is sent to swimming pools (petroleum lagoons) which, being mostly outdoors, receive rainwater, which generates a decrease in temperature and causes greater stability of the emulsion, increasing the apparent viscosity and the content of water and sediments (BS&W).

Oily waste has become an environmental liability causing hazards and risks associated with transportation, treatment, and final disposal. According to international regulations (Louisiana 29B), this waste is considered hazardous, which is why its disposal is mandatory. By not making an appropriate final disposal, damage to communities and the environment can be generated. In addition to the above, the treatment and final disposal of this waste implies for the operating company high costs associated with the obligations contained in the regulations applicable to said treatment.

In Colombia, the final disposal of oily waste has been carried out through bioremediation processes or in specialized treatment plants. However, these treatments require high investments in infrastructure, maintenance, and operation. In this regard, it is important to highlight that the recovery of oil from oily waste by some of these treatments, ranges from 0% to 7%.

Until a few years ago, due to the price of the oil barrel, this oily waste was not considered to be recovered by the operating companies. However, in view of the current fluctuation in the barrel price, the oil industry has focused on the search for new technologies aimed at recovering crude oil at low costs.

Regarding patents, the following state of the art applications are found: CA2708368, WO2008130214, MX2010012348A, US2011282125 (A1), and RU2008101553 (A).

Although several oil recovery processes are disclosed in the state of the art, it is necessary to develop more efficient and advanced processes and products to obtain higher percentages of oil recovery from production waste.

OBJECTS OF THE INVENTION

As a first object, this invention discloses a diluent and dispersing formulation of oily waste for oil recovery.

As a further object, this invention describes the process of recovering crude oil using a method of dilution and dispersion of the oily waste generated in the oil production process.

The objects referred above, as well as the additional objects that may be applicable, will be exposed in detail and thoroughly in the descriptive chapter that appears below, which will be the basis of the claiming chapter.

DETAILED DESCRIPTION OF THE INVENTION

Figure 1:
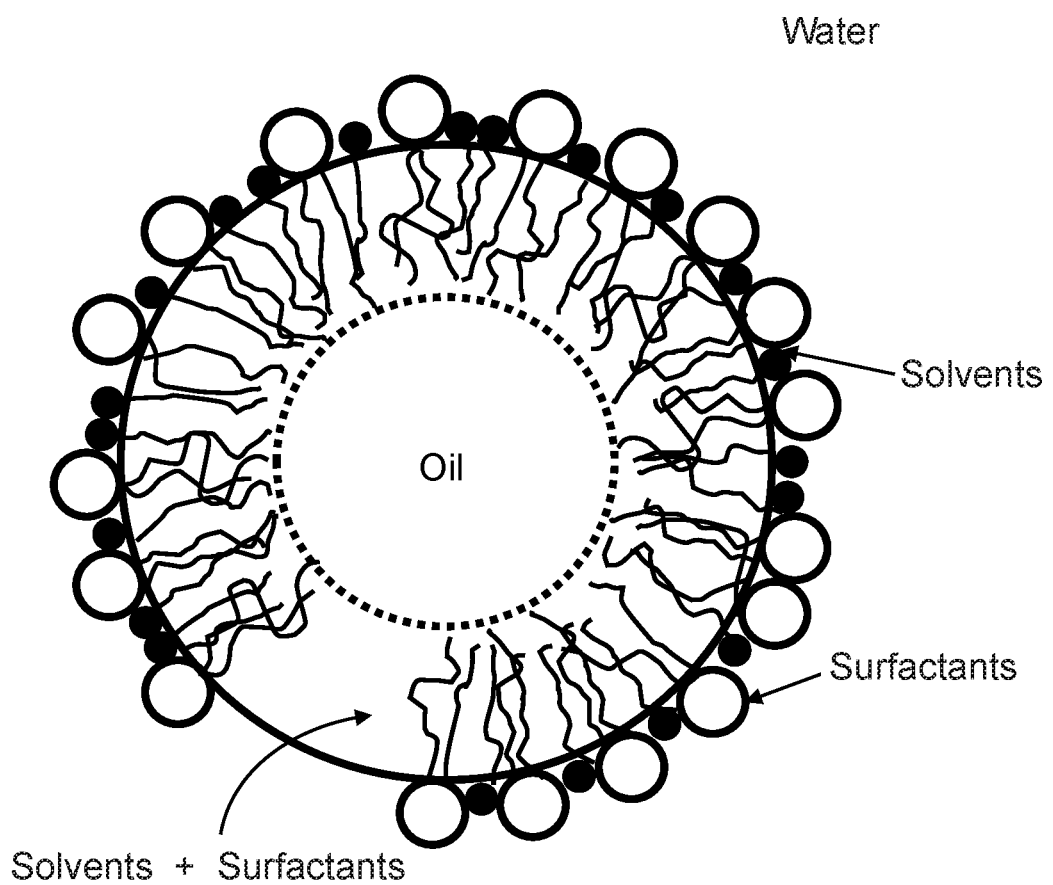
FIG. 1 is a graphical representation of the molecular structure of a micelle in oil/water emulsion, wherein the solvent and the surfactant act on an emulsifying agent, allowing the separation of water.
Figure 2:
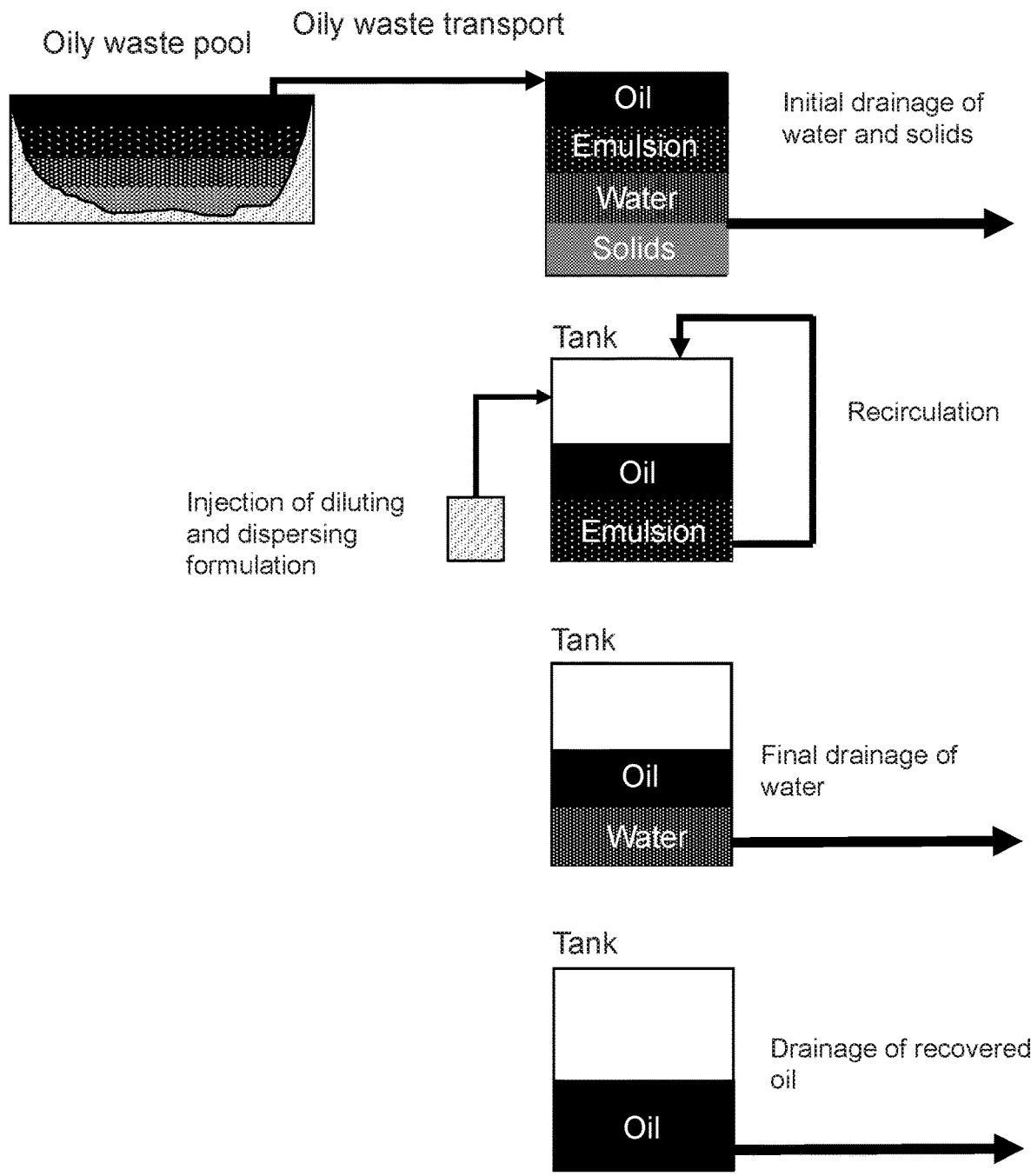
FIG. 2 is a diagram of the method of oil recovering from oily waste by using the present diluent and dispersing formulation.

Before presenting the detailed description of the invention, the definitions of some terms are included in order to clearly and concisely identify the scope thereof.

The term "diluent" should be understood as a characteristic of the formulation that is the subject of the patent application, which causes the dilution of the heaviest molecular compounds present in oily waste, bringing it to a more liquid state, allowing integration with lighter hydrocarbons.

The term "dispersing" should be understood as a characteristic of the formulation that is the subject of the patent application, which breaks the surface tension at the interface of hydrocarbon, water, and solids that make up the oily waste.

The term "oily waste" should be understood as a semi-liquid waste derived from industrial processes and treatment of production waters of the oil industry.

The term "surfactant" should be understood as a compound containing polar and non-polar parts, that acts by means of interface tension on the contact surface between two immiscible liquids. In the present invention, the surfactant disperses the inorganic and organic compounds of the oily waste.

The present invention discloses a diluting and dispersing chemical formulation of oily waste from oil production, that achieves the recovery of crude oil by diluting high molecular weight hydrocarbon rings present in oily waste in general, generated during the oil production process.

This waste, considered by international regulations as dangerous, is characterized by the stability of the emulsion of water, oil, and solids. The stability of the emulsion is affected by emulsifying agents such as asphaltenes, resins, fine solids, soluble organic acids, and other fine particles.

The chemical composition of the oily waste varies depending on the type of oil produced and the production scheme. The physical properties of this oily waste, such as density and viscosity, can vary significantly depending on their chemical composition, the type of oil produced, the location, and the collection time of the sample.

The diluent and dispersing formulation breaks the stable emulsion that characterizes this type of oily waste, by dispersing the inorganic elements (sediments and water) present in said waste.

The diluent and dispersing formulation enables the movement of oily residues, breaking millions of particles (micelles), wherein the oleophilic part of the surfactants forms a stable bond with the hydrocarbon chain and consequently encapsulates the oil particle, allowing the release of substances other than hydrocarbons.

In the stable state (stillness of liquids), these oily residues try to homogenize again, but due to the action of the surfactants, that is not possible, which consequently leads to the separation of organic and inorganic substances, thus achieving two interfaces: the first (superficial) of oil, and the second (bottom) of water with salts and inorganic solids.

The main physical and chemical properties of the diluent and dispersing of oily waste, and their respective performance in the formulation are described below.

First, the composition comprises linear sulfonic acid, which is an anionic surfactant (a negatively charged functional group in the molecule, associated with a cation that keeps the compound in balance, characterized by having an aliphatic chain at the non-polar end of the surfactant. Additionally, it has a benzene (aromatic) ring and a sulfonate group. The general formula would correspond to $CnH2n+1-C6H4-SO3-Na+$ The linear sulfonic acid is an effective dispersing element, forming micelles between the hydrophilic heads (presence of sulfonate) dissolved in water, while the hydrophobic tails leave the aqueous phase (alkyl chain).

Also, it is highly soluble in water when the alkyl chains have between 10 to 13 carbon atoms, and is soluble in solvents when the alkyl chains have more than 13 carbon atoms.

Therefore, the function of the linear sulfonic acid is to break the emulsion (oil/water) that is present in the oily residues, and help to separate the inorganic matter present in them (water, salts, clays).

Nonyl phenol is a non-ionic surfactant that has an aliphatic (non-polar) chain and a group consisting of an ethoxylated (polar) alcohol. The general formula would correspond to $C15H24O+n$ moles.

With this ethoxylated compound, a hydrophilic and lipophilic balance (HLB) is maintained. For that, the HLB value was used. According to that, surfactants with HLB values between 1-9 are more soluble in solvents and those with HLB values between 10-18 are more soluble in water.

In the formulation, the HLB 13 value was used because this value corresponds to an oil/water emulsifier, which is chemically absorbed at an interface, reducing the surface tension or the interface tension of the fluids and solids contained in the oily waste, and also leading to separate inorganic and organic waste.

Butyl glycol is a solvent capable of mixing with water and many paraffinic, aromatic solvents, ethers, and alcohols. Due to these properties, it is also considered a surfactant. The general formula of it would correspond to $C6H14O2$.

The diluent property of butyl glycol helps to thin many of the resins that are present in oil and at the same time helps in the rapid dehydration of oily waste.

It also acts as a surfactant, thanks to its affinity for solvents and water, breaking even more the surface tension, so facilitating the transport and fluidity of oily waste. Additionally, its linear structure is a determining factor in the biodegradability of the diluent and dispersing of oily waste.

Dimethylbenzene (xylol) is an aromatic class solvent, whose contribution to the formulation is that it is able to dissolve high molecular weight compounds, which are commonly found in oil of countries such Colombia.

The general formula would correspond to $C8H10$. It has the following characteristics and provides the following advantages in the formulation:

a) It is a hydrophobic solvent having the ability to dissolve many organic substances.
b) It is a hydrophobic solvent that has only affinity to non-polar structures, such as petroleum.
c) In its process of integration with oil, it dilutes the heaviest compounds of oil.
d) Being a direct distillate of oil, it does not affect it negatively.
e) It dilutes surfactants by reducing their viscosity and promotes penetration into oily waste, so that surfactants can act.

Kerosene is a petroleum distillate with a fairly complex composition, since it is a mixture of several organic compounds, among which paraffins, olefins, cycle-paraffins, and aromatic stand out. Due to this blend, there is no defined formula, but there is a range for carbon atoms (C10-C16).

Table 1 shows the raw materials that constitute the formulation, with their concentrations by volume:

TABLE 1

| Chemical Composition of the Formulation | |
| --- | --- |
| Raw materials | % Quantity |
| Linear sulfonic acid | Between 1-8% |
| Nonyl phenol | Between 9-13% |
| Butyl glycol | Between 8-20% |
| Kerosene | Between 15-45% |
| Raw materials | % |
| Dimethylbenzene (Xylol) | Between 15-45% |
| Blue methylene dye | 0.007% |

Regarding the physicochemical characteristics, the formulation has a boiling point of 138-144° C. at 1 atmosphere (1 standard atmosphere), is insoluble in water, and has a flash point of 38° C.

The product, according to a study carried out by the Instituto Colombiano de Petróleo (ICP) (Colombian Petroleum Institute), was also classified as an excellent degreaser, after evaluating the following parameters:

Effectiveness of the product.
Product risk level.
Technical sheet according to ICONTEC 4435.

General review of the MSDS data sheet.

Effectiveness tests performed at the laboratory level, evaluating performance and ecotoxicity.

Corrosivity tests.

In relation to the second object of the invention, which discloses a method for oil recovery in oily waste by the diluent and dispersing formulation, the method comprises the steps shown below:

a) Collection. Oily residues are stored in collection centers which, when are located outdoors, generate high environmental impact. They can also be stored in facilities (equipment) such as Frac Tanks, Catch Tanks and, in general, in any facility with storage capacity.

Taking into account the above, if the oily waste is stored in pools, it is extracted with either pneumatic double diaphragm pumps or a vacuum truck for collection at any available facility that has a loading and unloading unit to perform the treatment with the diluent and dispersing formulation of oily waste. If the oily waste is stored in facilities, the treatment is carried out in the same collection center.

b) Once the oily residues collection center is identified, the diluent and dispersant formulation is applied, similarly to the treatment in the following form:

Decantation. Once the oily waste has been collected at the facilities mentioned above, it is left in decantation for one hour where, due to differences in density and gravitational forces, the free water and solids precipitate at the bottom of the treatment tank.

After that hour, the extraction of solids and free water are carried out by the drain valve, leaving the oily waste with a lower content of water and sediments.

Characterization of oily waste. Once the drainage of solids and free water has been performed, the characterization of oily waste is carried out, taking into account the following main parameters: water and sediment content (BS&W) and API (American Petroleum Institute) gravity. That is done in order to determine the content of oil present in oily waste and its classification according to its API gravity (light: oil with an API gravity greater than 31.1 degrees; medium: oil with an API gravity between 29.9-22 degrees; heavy: oil with an API gravity between 21.9-10 degrees; and extra heavy: oil with an API gravity equal to or less than 10 degrees).

Dose of the diluent and dispersing formulation. Taking into account the characterization of the oily waste, the dose of the diluent and dispersing formulation to be used is determined. Depending on the oil content and its API gravity, the dose range is between 1.25% and 3.00%. Once the dose has been determined, the treatment tank is injected with the help of the vacuum truck or a double diaphragm pneumatic pump. The diluent and dispersing formulation comprises the following components:

| Linear sulfonic acid | Between 1-8% |
| --- | --- |
| Nonyl phenol | Between 9-13% |
| Butyl glycol | Between 8-20% |
| Kerosene | Between 15-45% |
| Dimethylbenzene (Xylol) | Between 15-45% |

Recirculation. Afterwards, with the help of a pneumatic, electric, or combustion pump, the recirculation is performed by loading and unloading the oily waste with the diluent and dispersing formulation, for two hours. The above is done with the purpose of reaching the homogenization of the mixture, ensuring the interaction of the diluent and dispersing formulation with the oily waste.

Decantation. With the active principle of the diluent and dispersing formulation, the separation and stratification of the three phases present in the emulsion, that is, oil, water, and sediments is achieved. The decantation time takes two hours after recirculation. After this time, drainage is done by the discharge valve used for water and sediments released by the diluent and dispersing formulation.

c) Transfer. Finally, the characterization of the oil recovered is performed, obtaining a water and sediment content (BS&W) of 2-5% for in-line treatment systems, and of 10-14% for the treatment of contingency pools. According to these results, the injection to the tank is arranged at a predefined rate as per the current parameters, so that the established oil specifications are not modified.

The examples described below are presented in order to describe the preferred aspects of the invention, but do not constitute a limitation on the scope thereof.

Example 1

The preparation of the formulation is carried out by mechanical blending of its elements in a mixing tank, which can be any vessel with a stirring system.

This stirring system works mainly by a motor, which converts electrical energy into mechanical energy, causing the stirrers to rotate and produce the mixture of the components added into the tank.

Example 2

Treatment carried out in el Bloque Cubarral, Campo Castilla, Ecopetrol.

The treatment of 39,536 barrels (1,660,512 gallons) of oily waste from a contingency pool was carried out in a facility located in el Bloque Cubarral (Frac Tank). The parameters obtained were an initial BS&W (water and sediment content) of 50% and an API (American Petroleum Institute) gravity of 10.5 degrees, corrected. After the application of the diluent and dispersing formulation, the parameters obtained were in a range of 13 to 16% for BS&W and 13.5 degrees for API gravity, corrected.

In this treatment, the steps described below were executed:

1. Collection. The oily waste was stored in a contingency pool, generating a high environmental impact because it was outdoors. The oily waste was extracted with a vacuum truck and then transported to Frac Tanks, which were situated around the pool to perform the on-site treatment.

2. Application of the diluent and dispersing formulation. Once the collection center of the oily waste was identified, the application and treatment of the oily waste was carried out with the subject of the invention—the diluent and dispersing formulation—, as follows:

a) Decantation. Once the oily waste is collected in the Frac Tanks, it is left there in decantation for one hour where, by means of difference on gravitational forces and densities, the free water and solids precipitate at the bottom of the treatment tank.

After this period, the extraction of these solids and free water is done by the discharge valve of the Frac Tank, leaving the oily waste with a lower content of water and sediments.

b) Characterization of oily waste. Once the drainage of solids and free water is executed, the characterization of the oily residues was performed, achieving results of 35-50% for water and sediment content (BS&W), and an API gravity of 10.5-12 degrees.

c) Diluent and dispersing dose. Taking into account the characterization of the oily waste, the diluent and dispersing dose to be used is determined. Based on the oil content and the API gravity obtained, a dose of 3.00% was determined. Once the dose was determined, the injection was made to the Frac Tank with the help of the vacuum truck or a pneumatic double diaphragm pump.

d) Recirculation. Afterwards, with a positive displacement pump, recirculation was carried out using the loading and unloading line of the Frac Tank for two hours. The above was done with the purpose of reaching the homogenization of the mixture and to ensure the interaction of the diluent and dispersing formulation with the oily waste.

e) Decantation. With the active principle of the diluent and dispersing formulation, the separation and stratification of the three phases present in the emulsion, that is, oil, water, and sediments is achieved. The decantation time takes two hours after recirculation. After this time, drainage is carried out by the discharge valve used for water and sediments released by the diluent and dispersing formulation.

3. Transfer. Finally, the characterization of the oil recovered is carried out, obtaining a water and sediment content (BS&W) of 13-16% and an API gravity of 13-13.5 degrees. According to these results, the oil recovered with a pneumatic double diaphragm pump at a rate determined by the operator is arranged to be injected, so that the established oil specifications are not modified.

Under the referred conditions, of the 39,536 barrels of oily waste collected, which correspond to a total of 19,768 barrels of oil that could be recovered, the oil recovery was 14,660 barrels, equivalent to a recovery rate of 74.16% of the oil susceptible to be recovered and to a recovery rate of 37% of the total oily waste treated.

Example 3

Treatment carried out in Monterrey, Estación el Porvenir, Ocensa.

The maintenance of an oil storage tank with a nominal capacity of 50,000 oil barrels and a remnant of 2,000 barrels of oily waste at the bottom was carried out.

Taking into account the characterization of the oily waste and efficiency curves, it was possible to determine a dose of 0.5% of the diluent and dispersing formulation, due to the high oil content.

Finally, with the referred dose and the mechanical homogenization of the mixture, 1,900 oil barrels were recovered, equivalent to a 95% rate of recovery.

Additionally, the active ingredient allows the viscosity to be reduced considerably and raises the API gravity degrees, generating an increase in the oil recovered because the product does not evaporate and is integrated into the hydrocarbons. Currently, the products on the market act only as diluents or as dispersants.

The formulation of the present invention constitutes a diluent and dispersing product of oily waste, meeting the purpose of diluting and dispersing the oily waste in a single formulation.

Example 4

The different uses and applications of the present invention, which is a diluent and dispersing formulation of oily waste, are embodied in procedures that involve the development of the following activities:

Oil recovery from oily waste generated in maintenance of hydrocarbon storage tanks, oil transport machinery, oil spilling contingencies.

Degreasing and cleaning of storage tanks and oil treatment.

Dilution of accumulations of high molecular weight hydrocarbons generated in transport pipelines and all kinds of facilities within the oil industry.

Treatment of flocks or oily waste from the calibration runs of pipe inspections in oil pipelines and/or multiproduct pipelines.

Stimulates exploitation of wells since it solves the damage caused by the deposition of paraffins and asphaltenes.

In fact, the application of the diluent and dispersing formulation of oily waste has been implemented in cleaning and degreasing of storage tanks, achieving the dilution and dispersion of the oily waste stored at the bottom of the tank, recovering up to 90% of the oil present there. Moreover, it has been used in cleaning and unclogging of pipes affected by the deposition of high molecular weight hydrocarbons, such as asphaltenes, resins, and paraffins. Due to the dilution achieved on this residues, it was possible to unclog and clean the affected pipes.

Although the present invention has been described with the preferred embodiments shown, it is understood that modifications and variations that retain the spirit and scope of this invention are within the scope of the attached claims.

The invention claimed is:

1. A formulation for oil separation and recovery from oil waste resulting from oil production, comprising a mixture of linear sulfonic acid, nonyl phenol, butyl glycol, kerosene, and dimethylbenzene, wherein the mixture is designed for recovery of crude oil after extraction during an oil production process.

2. The formulation according to claim 1, wherein the concentration of the components is the following:

| | |
|---|---|
| Linear sulfonic acid | Between 1-8% v/v |
| Nonyl phenol | Between 9-13% v/v |
| Butyl glycol | Between 8-20% v/v |
| Kerosene | Between 15-45% v/v |
| Dimethylbenzene (Xylol) | Between 15-45% v/v. |

3. The formulation according to claim 1, further comprising 0.007 % v/v methylene blue dye.

4. The formulation according to claim 1, characterized by having a boiling point of 138 to 144° C. at 1 atmosphere.

5. The formulation according to claim 1, characterized by being insoluble in water.

6. Method for oil separation and recovery from oily waste resulting from oil production, characterized by comprising the following steps:
provide a load of oily waste derived from oil production;
add to said oily waste a formulation comprising a mixture of linear sulfonic acid, nonyl phenol, butyl glycol, kerosene, and dimethylbenzene (xylol);
mixing of said oily waste and the formulation;
allow separation of a phase containing oil from a phase containing water and sediments; and
recover the phase containing oil.

7. The method according to claim 6, wherein the formulation components have the following concentrations:

| | | |
|---|---|---|
| Linear sulfonic acid | Between 1-8% v/v | |
| Nonyl phenol | Between 9-13% v/v | |
| Butyl glycol | Between 8-20% v/v | |
| Kerosene | Between 15-45% v/v | |
| Dimethylbenzene (Xylol) | Between 15-45% v/v. | |

8. The method according to claim 6, wherein the fact that the dose range of the formulation applied to the oily waste is between 1.25 % v/v and 3.00 % v/v.

9. The method according to claim 6, wherein the mixing of oily waste with the formulation is carried out by recirculation.

10. The method according to claim 6, characterized by the fact that the separation of the phase containing oil from the phase containing water and sediments is carried out by decantation for two hours.

11. A formulation for oil separation and recovery from oily waste resulting from oil production, comprising a mixture of linear sulfonic acid, nonyl phenol, butyl glycol, kerosene, dimethylbenzene, and methylene blue dye.

12. A formulation for oil separation and recovery from oily waste resulting from oil production, comprising a mixture of linear sulfonic acid, nonyl phenol, butyl glycol, kerosene, and dimethylbenzene, having a boiling point of 138 to 144° C. at 1 atmosphere.

* * * * *